US006524803B2

(12) United States Patent
Overney et al.

(10) Patent No.: US 6,524,803 B2
(45) Date of Patent: Feb. 25, 2003

(54) DECONVOLUTION METHOD AND APPARATUS FOR ANALYZING COMPOUNDS

(75) Inventors: Gregor T. Overney, Sunnyvale, CA (US); David T. Peterson, Scotts Valley, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 124 days.

(21) Appl. No.: 09/741,982

(22) Filed: Dec. 19, 2000

(65) Prior Publication Data

US 2002/0117615 A1 Aug. 29, 2002

(51) Int. Cl.[7] ................................................ G01N 33/53
(52) U.S. Cl. ......................... 435/7.1; 250/282; 250/281
(58) Field of Search ............................... 435/7.1, 287.1; 250/282, 281

(56) References Cited

U.S. PATENT DOCUMENTS 6,015,667 A 1/2000 Sharaf ........................... 436/6
6,284,459 B1 * 9/2001 Nova et al. .................... 435/6
6,329,146 B1 * 12/2001 Crooke et al. ................. 435/6

FOREIGN PATENT DOCUMENTS

WO WO 00/05760 2/2000

* cited by examiner

*Primary Examiner*—Bruce Anderson
*Assistant Examiner*—Nikita Wells

(57) ABSTRACT

A mass spectrometer system analyzes a sample with the aid an associated computer system or processor which utilizes a relatively small compound deconvolution data library. The deconvolution library has a specific predefined order. The specific order of the compounds in the library is established based on predetermined knowledge of the sample being tested by the mass spectrometer. A deconvolution technique utilized by the computer system automates a deconvolution technique that would be utilized by an experienced process chemist for a similar sample and associated fragmentation or cracking pattern. The deconvolution technique steps through the deconvolution library's order of compounds and compares each compound's stored spectral data with the sample's spectrum. If it is determined that a compound's spectrum is found in the sample's spectrum, then at least one complete peak associated with the found compound's spectrum is removed from the sample's spectrum.

16 Claims, 2 Drawing Sheets

DECONVOLUTION METHOD AND APPARATUS FOR ANALYZING COMPOUNDS

BACKGROUND OF THE INVENTION

1. Field of the Invention

The present invention relates to a method and apparatus for the deconvolution of spectra, or of fragmentation or cracking patterns. More particularly, the present invention is related to a deconvolution technique operating in conjunction with a mass spectrometer.

2. Description of Related Art

Regardless of the mass spectrometer used, generally whenever a mass spectrum of compound is collected it is often up to an experienced process chemist to analyze and interpret the mass spectrum by hand. A mass spectrum can also be used to determine a fragmentation pattern or cracking pattern. The process chemist attempts to match the mass spectrum of the unknown compound against known compound spectra. A process chemist may require extended amounts of time to deconvolute (i.e., interpret) a mass spectrum and determine the elements or molecules that are in the unknown sample. Furthermore, the process chemist must remove or manually “filter out” all known or determined information from the mass spectrum as the deconvolution process continues.

During manufacturing of highly pure substances, such as silicon wafers or semiconductor devices, it is important to determine the composition of the wafer environment in order to detect problems with the process. This must be done quickly to maximize the value in a manufacturing process.

Thus, what is needed is a system analytical instrument that incorporates a methodology adapted to deconvolute a mass spectrum or fragmentation pattern using an intuitive approach that is similar to that of an experienced process chemist. Such a system may be able to test substances in a manufacturing process in a timely manner such that the manufacturing process is not significantly slowed and alarms can be exhibited when predetermined substances (contaminants) are found within the manufacturing process. The system may be associated with a mass spectrometer.

SUMMARY OF THE INVENTION

An exemplary embodiment of the present invention provides a mass spectrometer with a computer aided methodology for analyzing a sample and its associated fragmentation or cracking patterns. A deconvolution compound data library is selected by a user to be utilized by the computer system. The deconvolution library comprises compounds in a specific or predetermined order. Each compound entry includes an ionization energy for the compound and associated peaks or m/z values with associated abundance values. The compound library may have a few to as many as about 150 compound entries contained therein. The specific order of the compound library is very important because it mimics the deconvolution process that an experienced process chemist would utilize to deconvolute a fragmentation pattern from a sample taken from a known or somewhat known process or substance. The computer system deconvolutes the fragmentation pattern using the ordered compound library such that if a “fingerprint” of a compound from the compound library is found in the fragmentation pattern, then at least one full peak (m/z value and its associated abundance value) is removed from the fragmentation pattern prior to searching for the existence of the next compound from the compound library in the fragmentation pattern. Found compound remainder values can also be removed from the fragmentation pattern.

The exemplary embodiment can provide indications, such as visual or audible alarms, if a compound that is considered a contaminant is found in the fragmentation pattern. The exemplary embodiment is especially useful in manufacturing processes wherein purity is important. Examples of such processes include physical vapor (PVD) deposition and chemical vapor deposition (CVD), utilized, for example, in semiconductor manufacturing. An exemplary embodiment of the present invention can be incorporated into such a manufacturing process and can monitor purity and quality criteria associated with the process or manufactured items.

BRIEF DESCRIPTION OF THE DRAWINGS

Various objects and advantages of this invention will become apparent and more readily appreciated from the following description of the presently preferred exemplary embodiments, taken in conjunction with the accompanying drawings, of which.

DETAILED DESCRIPTION OF THE PREFERRED EXEMPLARY EMBODIMENTS

Descriptions of preferred exemplary embodiments of the present invention will now be described with reference to the accompanying drawings. This invention may, however, be embodied in many different forms and should not be construed as limited to the embodiments set forth herein; rather, these embodiments are provided so that the disclosure is thorough and complete and will convey the pertinent aspects of the invention to those skilled in the art.

Figure 1:
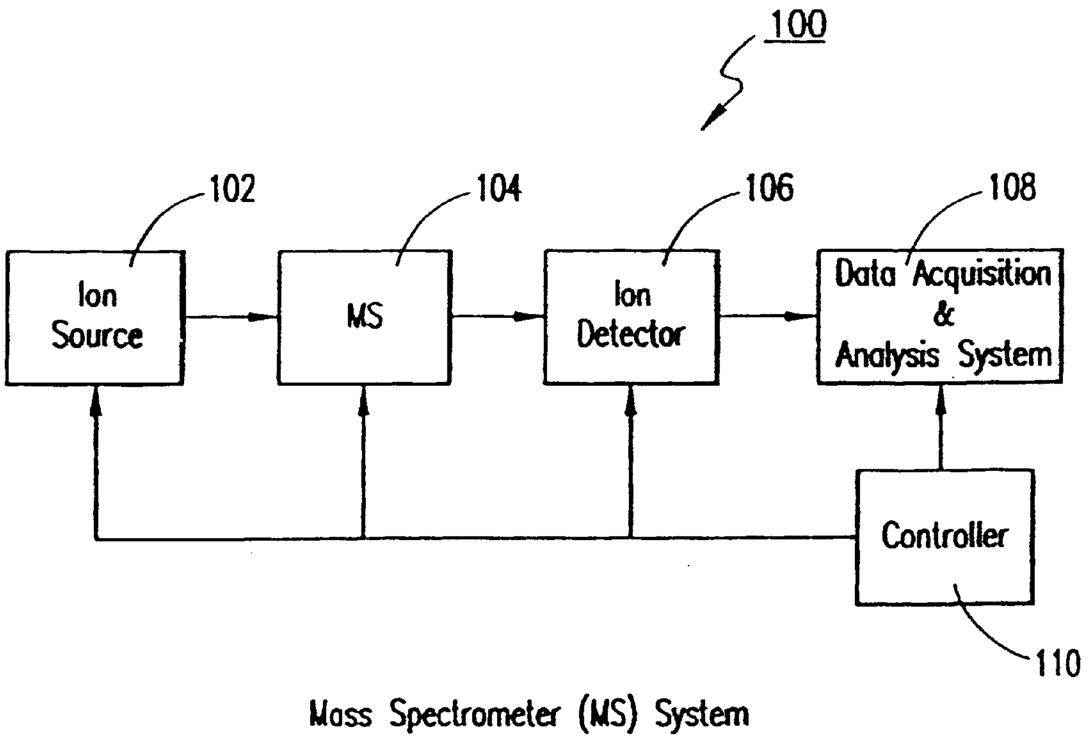
FIG. 1 depicts a mass spectrometer system in accordance with the present invention.

A mass spectrometer system 100 in accordance with present invention is depicted in FIG. 1. An exemplary mass spectrometer 100 could be any type of mass spectrometer. An exemplary mass spectrometer 100 may include various components common to mass spectrometers. Such components include an ion source 102. A mass spectrometer section 104 provides a means for affecting the flight paths or flight times of the ions. Ion mirrors, lenses and optics which utilize electric and/or magnetic fields are used in various types of exemplary mass spectrometer sections.

An ion detector section is used to produce a response that is proportional to the number of ions the detector detects. A data acquisition and analysis system 108 (DAAS) receives signals from the detector and aids a process scientist in understanding the composition of a sample that produces a fragmentation pattern detected by the detector 106. The data acquisition and analysis system may include electronics for sampling and/or data acquisition, microprocessors/microcontrollers, software or firmware, digital signal processing (DSP) circuitry, power supplies, memory devices, and display devices and user interface controls. Furthermore, a controller 110 which operates to set up and synchronize the workings of each part of the mass spectrometer system 100 is included and connected to the various portions of an exemplary mass spectrometer 100.

An exemplary mass spectrometer is utilized to produce a mass spectrum which is derived from analog or digital signals. (Signals can be derived from pulse counting; i.e., single-ion counting.) The composition of the mass spectrum is to be analyzed. To do so, the unknown spectrum is compared against an exemplary deconvolution library of known spectra stored in the memory of the data acquisition and analysis system 108. Unlike in the prior art of spectra stored in libraries and related library searches, an exemplary deconvolution algorithm or method of analyzing the mass spectrum of the present exemplary embodiments depends, in part, on the specific order of the compounds in the library of known spectra of compounds. Changing the order of use of the compounds in the library will affect the outcome of the compound identification process used on the unknown mass spectrum. Furthermore, the exemplary deconvolution process operates with a small deconvolution library file having preferably only ten (10) to one hundred-fifty (150) compounds in the library. By ordering (using) the library compounds in a predetermined order and only using a limited number of library compound entries, the exemplary mass spectrometer systems can be made to analyze an unknown fragmentation pattern in real-time using an intuitive approach that resembles the approach of an experienced process chemist. The exemplary mass spectrometer system performs the analysis in real-time without the aid of the process chemist.

During physical vapor deposition (PVD) or chemical vapor deposition (CVD) process monitoring, processes used in the fabrication of silicon based integrated circuits, an exemplary mass spectrometer can be utilized to notify a user of alarm conditions. Alarm conditions are determined based on complete mass spectral analysis. An alarm condition may exist when certain substance or contaminants are present or present in a predetermined amount in the PVD or CVD process. Automation of the monitoring process with a mass spectrometer decreases cost and increases production quality by providing an accurate and timely quality control feedback loop.

To automate PVD or CVD process monitoring, the collected spectra must be deconvoluted at a rate that meets or exceeds the spectrum acquisition rate of the mass spectrometer. This type of deconvolution (i.e. deconvolution of spectral data at least as fast as a mass spectrometer can create spectral information) is called "on-the-fly" deconvolution. To accommodate deconvolution on-the-fly it is important that the exemplary deconvolution process be capable of distinguishing relevant and irrelevant deconvolution results in order to avoid setting an alarm state when contaminants are not affecting the PVD or CVD process that is being monitored.

The methodology of the exemplary process provides suitable technology for a manufacturing process monitoring system that is capable of verifying alarm conditions based on species. Species are compounds with abundance values and corresponding m/z values.

Prior conventional systems which utilized linear algebra or probability matching tended to trigger process contamination alarms that when closely analyzed were false alarms based on statistical interpretation of data. False alarms lead to expensive process shutdowns and are unacceptable in wafer fabrication facilities. Furthermore, prior art, simplistic procedures for computer-matching of mass spectra with "canned" spectral data are only aids to, and not replacements for, a skilled interpretation of mass spectra by an experienced process chemist.

The exemplary method and apparatus incorporates an algorithmic approach that orders the compounds in the system's compound library of known spectra (the deconvolution library) in a specific predetermined order. The predetermined order of the compound spectral data is adjusted and organized by, for example, a process chemist for each given PVD or CVD process. As a process and the possible contaminants to the process are better understood over time, a fine tuning of the order and compounds in the deconvolution library can increase accuracy and enhance the deconvolution results.

As an aside, an example of a unsuitable deconvolution algorithm is as follows: It is understood that all mass spectra consist of mass assigned integral masses distributed over a mass range of N total masses. A spectrum is a set of abundance values, S as a function of m/z values. To simplify the notation, j will be used instead of m/z.

S(j) is a spectrum of interest. Let $C_i(j)$ be a species in a data base. A species is a compound with abundance values and corresponding m/z values. Also, $C_i(j)$ is called a spectrum of a given known compound. The total number of spectra in the species database is n. The species data base is not ordered in an order relevant to the specific sample being tested in the mass spectrometer. Let $a_i$ be the abundance of $C_i(j)$. The $a_i$ can be considered scaling factors. (It must be assumed that the mass spectrometer being used records relative abundance with a good degree of accuracy.) Since S(j) is assumed to be linear combination of given compounds, it follows that $S(j)=\Sigma a_i*C_i(j)$. Assuming that the species database contains all the possible spectra cases for the spectrum of interest, then it therefore forms a complete basis to represent all possible S(j). (Note that this assumption is not realistic, but simplifies this explanation. In practice, this unsuitable algorithm uses a linear fit with a set of uncertainty values from which it calculates statistically based confidence levels.) The summation (Σ) is carried out over all known compounds in the data base. Utilizing matrix notation, this leads to S=CA. This algorithm determines the vector A. One can determine from this example of an unsuitable deconvolution algorithm that the linear fit technique is only able to suggest the best spectral match between a sum of spectra in the species data base and the spectrum provided from the mass spectrometer.

The present exemplary method and apparatus implement a more direct approach that resembles, mimics, and substantially automates the process an experienced process chemist would use to deconvolute a fragmentation pattern. An exemplary embodiment of the present method of deconvolution acts as a "compound-sieve" in that, in effect, it gradually filters out all the desired knowledge from a given input data histogram spectrum and further needs only a relatively small deconvolution spectra data base comprising data for only ten (10) to one hundred-fifty (150) compounds. An exemplary embodiment preferably uses histogram or mass-assigned data to which a peak-picking algorithm has been applied.

The exemplary method and apparatus focus on compound identification techniques. A library file for each compound contains a fingerprint set of m/z values. At least one peak in the input spectrum that corresponds to a fingerprint peak is completely removed provided that all other fingerprint peaks are present. All contributions (scaled by relative abundance) to peaks in fingerprint and remainder are removed. Simply put, at least one complete histogram peak from the input spectrum is removed along with associated contributions to other peaks that are common with those in the spectra of other compounds. It is not preferred that relative contributions are calculated for "tiny" peaks in the histogram. The tiny peaks have very small signal-to-noise ratios relative to those of the larger peaks. Thus, the tiny peaks are preferably not considered in the determination of whether a specific compound is present in a given input data spectrum.

The preferred embodiment preferably determines that if a peak of a remainder is too large when compared to the corresponding peak height in the input data spectrum (after calculating relative abundance), the methodology of the present invention removes the total contribution of the peak, which has a certain m/z value, from the input spectrum. On the other hand, if the remainder is not too large relative to the corresponding peak height in the input data spectrum, only the appropriate contribution of the peak for the determined (found) compound is taken out. This exemplary technique ensures that as much spectral information of a found compound is removed from the input data spectrum as possible, but this technique avoids using peaks that have an undesirably small signal-to-noise ratio. If a single peak that belongs to a "fingerprint" of a compound is not present in the input spectrum, it is assumed in the exemplary embodiment that the compound is not part of the fragmentation pattern being deconvoluted.

As stated above, the exemplary embodiments require a relatively small deconvolution library comprising data for about ten to about one hundred-fifty compound entries in the library. The order of the library is extremely important because the order mimics an intuitive approach resembling the approach that would be used by an experienced process chemist for a similar deconvolution test situation. To understand a given spectrum, the experienced process chemist will try to identify all peaks, or contributions to peaks, that belong to known compounds, starting with the most likely to be present. He proceeds step by step, removing known peaks (or portions of peaks) and examining peaks that are left.

The deconvolution library comprises data in a predetermined and suitable file format. The data for each compound in the convolution library should include (1) the compound name; (2)the compound's ionization probability; and (3) one or more m/z abundance values used to identify the compound spectra (the fingerprint). Additional information (such as compound remainder information) can be included in the compound data. The additional information may include m/z abundance values that are not used to determine whether a compound is present in the input data spectra, but instead are used to remove peaks or portions of peaks from the input data spectrum when the compound is found to be present in the input data spectrum.

The workings of an exemplary compound analyzer are now described. A mass spectrometer data histogram (the input data spectrum) is generated via a mass spectrometer. The technique for analyzing the input data spectrum comprises a few basic events. First a computer system (e.g. a server, CPU, PLU, etc.) loads the deconvolution compound library into a memory. Next, the computer system, using the deconvolution compound library in the specific, predetermined order of the compounds, compares the library compound data with the input data spectrum, and removes compound spectra from the input data spectrum, one by one, in accordance with the library data for a found compound. The computer system may then remove labels (compounds without abundance values and only m/z values) and determine a residual.

Figure 2:
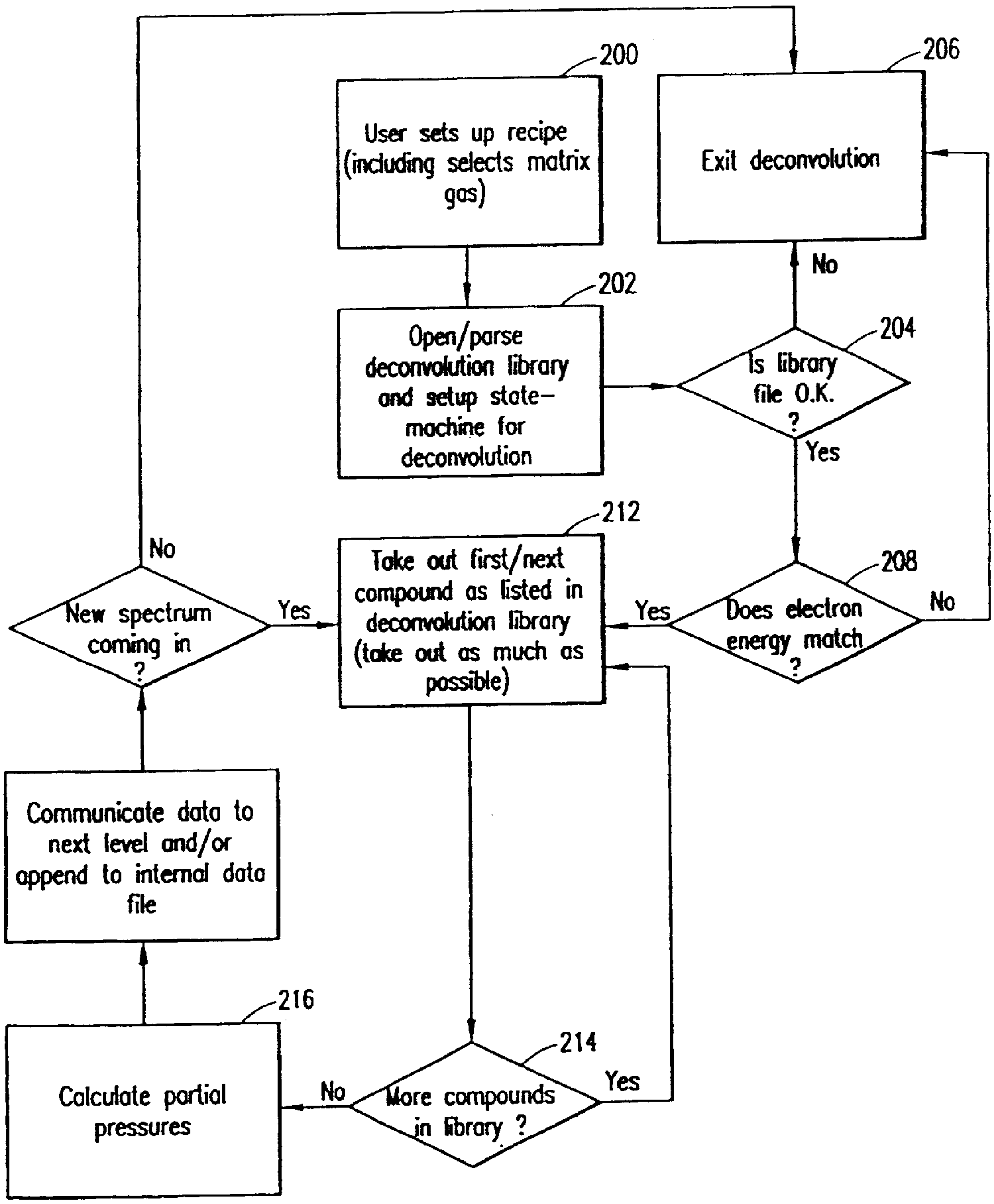
FIG. 2 depicts a method of deconvoluting a fragmentation pattern, mass spectrum or cracking pattern in accordance with the present invention.

Referring now to FIG. 2, an exemplary method in accordance with the present invention is depicted for deconvolution of a spectrum or fragmentation pattern. At step 200, the user sets up the program. In doing so, the user may define what PVD or CVD process is to be monitored (i.e. the user selects an appropriate deconvolution library for the compound sample). The user may also select an appropriate electron energy.

At step 202, the computer system opens a deconvolution library that is associated with the PVD or CVD process that is to be monitored.

At step 204, the computer system checks the format of the selected deconvolution library. If the deconvolution library is not successfully loaded or is not in the correct format an error flag is encountered and the deconvolution technique is ended at step 206. If the deconvolution library is successfully loaded and is without errors, then the electron energy to be used by the mass spectrometer is checked at step 208. The computer determines if the electron energy which is defined in the selected deconvolution library matches an electron energy that is set or was selected by the user to be used in the mass spectrometer. If the set energy and the deconvolution library required energy setting do not match, then the deconvolution method exits at step 206.

After the library is loaded and the electron energy is determined to be set correctly, then the deconvolution library, in the form of data, is moved into memory in a suitable format. A mass spectrometer provides an input data spectrum in the form of a suitable format for the computer system.

At step 212, the computer reads the first compound from the deconvolution library and compares its data file spectral information (its fingerprint) with the input data spectrum. If a spectral match occurs, indicating that the library compound spectra are present in the input spectrum, then the system removes portions of the input data spectrum histogram by calculating an appropriate multiplier associated with the given compound. The multiplier may be determined by: 1) check if complete "fingerprint" information is present; 2) if yes, find multiplier for each individual peak (divide each peak abundance by corresponding library relative abundance.); and 3) select smallest multiplier and scale all peaks in fingerprint accordingly. The computer system then may save the multiplier as a coefficient for the given compound. The technique for subtracting the deconvolution library data for the matched compound from the input data spectrum histogram includes subtracting fingerprint information. At least one entire histogram peak that is associated with the matched compound is subtracted. Again, fingerprint information is peaks that provide a clear indication that a specific compound is present. Then, the technique for subtracting the deconvolution library data subtracts remainder information (information that is not fingerprint information) that needs to be removed. A preferred mechanism for subtracting remainder information is as follows:

a) calculate multiplier $M_1$ for the fingerprint information without consideration for removal of remainder information. If $M_1$ is zero then the deconvolution library compound does not have its fingerprint in the input data histograph, and steps b, c and d below can be skipped. The multiplier is calculated, to allow the removal of as much of the input data histogram as possible for the given compound. $M_1$ may be calculated by: 1) check if complete "fingerprint" information is present; 2) if yes, find multiplier for each individual peak (divide each peak abundance by corresponding library relative abundance.); and 3) select smallest multiplier and scale all peaks in fingerprint accordingly.

b) calculate multiplier $M_2$ for fingerprint plus remainder. This may result in a different multiplier than $M_1$. $M_2$ is calculated the same as $M_1$, but instead use the entire spectrum (fingerprint plus remainder).

c) calculate $\sphericalangle : \sphericalangle = |M_{1-M2}|/M_1$ d) The closer $\sphericalangle$ is to zero, the more appropriate the information in the remainder is for determining whether the spectrum of given compound is present in the histogram data.

The value of $\sphericalangle$ is utilized with the deconvolution data thereby providing an indication of the quality of the resulting deconvolution. The calculation of $\sphericalangle$ can be excluded from the preferable deconvolution method if code/memory space is an issue or if the computer system's microprocessor or CPU is too slow.

e) Use $M_1$ (never $M_2$) multiplied by appropriate portion of the compound deconvolution compound data to subtract out appropriate peak portions from the input histogram data. If the adjusted compound remainder of a given peak is larger than the associated input histogram peak remove the entire peak.

Once the first compound, as listed in the deconvolution compound library, has been compared with the input histogram data; and if necessary, the appropriate compound fingerprint and remainder have been removed from the input histogram, then at step 214 the system determines if there are any more deconvolution compounds in the deconvolution compound library to be compared to the remaining input histogram.

If more deconvolution library compounds for comparison exist then step 212 is repeated for the next deconvolution library compound. Note that the sequence of the compounds in the deconvolution library is important because for the particular PVD or CVD process (or other mass spectrometer use) The library compounds are in an order that would be utilized by an experienced process chemist for the particular application/process. An experienced process chemist would first take the compound out that he is sure is present.

After all the deconvolution compounds in the compound library have been sequentially tested against the input histogram data and step-by-step removal of compound fingerprints and compound remainder has taken place, then the exemplary method calculates partial pressures at step 216.

Prior to discussing the calculation of partial pressures, a further clarification of the present and above discussed deconvolution method is exemplified. Using the notation [m/z; abundance], assume the input data histogram provided a fragmentation pattern of: [10; 234] [15; 126] [25; 58] [102; 22] [153; 66] [202; 50]and a current deconvolution compound library contained the following set of deconvolution compounds, each compound having an ionization efficiency followed by m/z and abundance values:

| | | | |
|---|---|---|---|
| "compound A" | "1.00" | [15; 100] | [153; 7] |
| "compound B" | "1.00" | [10; 17] | [25; 1] |
| "compound C" | "1.00" | [10; 50] | [102; 1] |

The first iteration of the exemplary deconvolution method results in a multiplier $M_1$ for compound A of 1.26. Multiply 1.26 by the compound A abundances and subtract the result from the input data histogram.

The resulting input data histogram is: [10; 234] [25; 58] [102; 22] [153; 57.18] [202; 50]

Note that this calculation will completely use up m/z=15 but not m/z=153. In any given iteration all of at least one [m/z; abundance] will be used up.

In the second iteration the multiplier $M_1$ for compound B is substantially 13.76.

Again, multiplying 13.76 by the compound B abundances and subtracting the result from the input data histogram provides:

[25; 44.24] [102;22] [153; 57.18] [202; 50] (note that all of m/z=10 was used up).

The third iteration yields a multiplier $M_1$ for compound C equal to zero (0) since there is no longer a value for m/z=10 available.

Thus, the results of the multipliers $M_1$ for compounds A, B and C are 1.26, 13.76, and 0 respectively. The total "species-considered" residual equals 173.42=(44.24+22+57.18+50). Since all of the ionization probabilities for the compounds were "1.00", then the multipliers are already adjusted.

If it is known that the total pressure associated with the total ion count (TIC) of 556 is 120 torr, then the partial pressure for compound A is 134.82/556*120 torr=29.1 torr.

The partial pressure for compound B=247.68/556*120 torr=53.46 torr.

For the species-considered residual the partial pressure=173.42/556*120 torr=37.49 torr. As expected, the addition of the individual partial pressures equals 120 torr.

From the above example, one can observe the importance of the order of the deconvolution compounds in the deconvolution compound library. For example, if compound A is listed after a compound D (defined as "1.00" [15; 100]) then nothing would be left in the input data histogram for compound A after compound D has been removed via the exemplary methodology.

Furthermore, it is noted that in actual laboratory circumstances it is rare that the relative ionization probabilities are all 1.00. Thus, calibration of the partial pressures is performed in step 216 of FIG. 2 and is as follows:

The calibration of partial pressures utilizes calibration parameters associated with the input data spectrum. Such a calibration could be performed by choosing a reference peak for a given matrix gas or by knowing the total pressure associated with the TIC. The calibration of the incoming input data spectrum is not part of the present invention. Furthermore, by default it is assumed that the residual has an ionization probability of 1.00. This assumption may not reflect the true nature of the residual.

Regardless, after the deconvolution method and technique of steps 212 and 214 have been applied, it is known relatively how much of each species (compounds with abundance values) is present in the input data spectrum. The following steps are required to calibrate the partial pressures with regard to ionization probability:

1) A correction factor $\lambda_C$ must be calculated for each found compound. A residual correction factor $\lambda_{residual}$ for the "species-considered" residual must also be calculated.

$$\lambda_C = I_C{}^* p(C)^{-1} / (\Sigma_i (I_{C(i)} \cdot p(C(i))^{-1} + I_{residual}{}^* p(C_{residual})^{-1})$$

$$\lambda_{residual} = I_{residual}{}^* p(C_{residual})^{-1}) / (\Sigma_i (I_{C(i)} \cdot p(C(i))^{-1}) + I_{residual}{}^* p(C_{residual})^{-1}),$$

where $I_C$ is the contribution to the TIC of the selected compound, p(C) is the ionization probability of the selected compound, and the summation $\Sigma_i$ is taken over all compounds that have been found (except the residual, which is considered separately).

2) If not otherwise specified, the residual always has an ionization probability of one. Using the total pressure for the TIC, the uncorrected partial pressures are calculated (assume ionization probabilities are one).

3) Multiply the uncorrected partial pressure values by the corresponding correction factor $\lambda_C$ in order to obtain the respective ionization probability corrected partial pressures (see example below).

4) Forward the corrected partial pressures to the computer system to determine if they are within a predetermined range. The predetermined range will aid in alarm condition verification for an exemplary PVD or CVD process.

To clarify the partial pressure calculation steps and referring to the above example, assume that the ionization probabilities for compounds A, B, and C are not "1.00" for each, but are instead "1.00", "0.50", and "0.10" respectively. Since the deconvolution process found there to be no contribution of compound C, the method can focus on the partial pressures for compounds A and B. Using the equations above:

$$\lambda_A = 134.82^*(1.00)^{-1} / (134.82^*(1.00)^{-1} + 247.68^*(0.5)^{-1} + 173.42^*(1.00)^{-1})$$

$$\lambda_B = 247.68^*(0.5)^{-1} / (134.82^*(1.00)^{-1} + 247.68^*(0.5)^{-1} + 173.42^*(1.00)^{-1})$$

$$\lambda_{residual} = 173.42^*(1.00)^{-1} / (134.82^*(1.00)^{-1} + 247.68^*(0.5)^{-1} + 173.42^*(1.00)^{-1})$$

Therefore, the ionization probability corrected partial pressure of compound "A" amounts to 120 torr $^*\lambda_A$=20.13 torr, for compound "B", it is 120 torr $^*\lambda_A$=73.97 torr, and for the "species-considered" residual, we obtain 120 torr $*\lambda_{residual}$= 25.90 torr. The total pressure amounts to 120 torr, as expected.

Various advantages are accomplished by one or more combinations of the above exemplary embodiments of a method and apparatus for deconvolution of a fragmentation pattern. The exemplary embodiments can be "fine tuned" to operate in specific environments such as a PVD or CVD process in order to warn of alarm conditions wherein contaminants are present in the prescribed process. Furthermore, the exemplary method can operate using techniques used by experienced process chemists, but in an automated fashion, decreasing the overall time required to deconvolute a fragmentation pattern. It would be appreciated by those skilled in the art that changes may be made to disclosed embodiments without departing from the principles and the spirit of the invention, the scope of which is defined in the appended claims:

What is claimed:

1. In a mass spectrometer system an automated method for analyzing a sample, said method comprising the steps of:

selecting a deconvolution library, said deconvolution library comprising a plurality of compounds in a specific order, each said compound comprising compound data;

comparing first compound data from said specific order with spectral pattern data from a mass spectrometer;

removing a portion of said spectral pattern data if said first compound data of a first compound is substantially found in said spectral pattern data, thereby creating a remaining spectral pattern data;

comparing next compound data from said specific order with said remaining spectral pattern data;

removing a portion of said remaining spectral pattern data if said next compound data is substantially found in said remaining spectral pattern data;

repeating said comparing a next compound data step and said removing a portion of said remaining spectral pattern data step until all said plurality of compounds have been compared in said specific compound order.

2. The method of claim 1, wherein said removing steps include removing at least one complete m/z and its related abundance value from at least one of said spectral pattern data and said remaining spectral pattern data.

3. The method of claim 2, wherein said removing steps include removing remainder associated with said substantially found compound from at least one of said spectral pattern data and said remaining spectral pattern data.

4. The method of claim 1, wherein said compound data for at least one of said plurality of compounds includes an ionization probability, a m/z value and an associated abundance value.

5. The method of claim 1, further comprising the step of calculating partial pressures of said substantially found compounds.

6. The method of claim 1, wherein said mass spectrometer is used to monitor a manufacturing process.

7. The method of claim 1, wherein said deconvolution library comprises between about 10 and about 150 compounds.

8. The method of claim 7, wherein said specific order of said deconvolution library is related to a predetermined scheme for analyzing said spectral pattern data.

9. A system for analyzing a spectral pattern created by a mass spectrometer comprising:

a first processor;

a computer readable medium electrically coupled to said first processor;

a plurality of instructions wherein at least a portion of said plurality of instructions are storable in said computer readable medium and further wherein said plurality of instructions are configured to cause a processor to:

initiate selection of a deconvolution library, said deconvolution library comprising predetermined compound entries in a specific order, each said compound entry comprising compound fingerprint data;

compare each of said compound fingerprint data in said specific order to spectral pattern data, said spectral pattern data comprising, at least, a plurality of m/z and abundance information;

determine whether said spectral pattern data includes said compared compound's fingerprint data;

remove at least one m/z and abundance information if said spectral pattern data includes said compared compound's fingerprint data;

remove remainder information associated with said compared compound's fingerprint data if said spectral pattern data includes said compared compound's fingerprint data.

10. The system of claim 9, wherein said plurality of instructions are further configured to cause the processor to calculate partial pressures associated with compounds having fingerprint data found in said spectral pattern.

11. The system of claim 9, wherein a plurality of said compound fingerprint data includes ionization probability information and at least one m/z value.

12. The system of claim 11, wherein said plurality of said compound fingerprint data further includes an abundance value for at least one of said m/z values.

13. The system of claim 9, wherein said specific order of said predetermined compounds is determined based on an expected sample type being used in said mass spectrometer.

14. The system of claim 9, wherein said system further comprises:

a mass spectrometer for providing said spectral pattern data for use by said first processor.

15. The system of claim 9, wherein said system is utilized in a manufacturing process in order to provide an indication that evidence of a predetermined compound fingerprint data is found in said spectral pattern data.

16. The system of claim 10, wherein said plurality of instructions are further configured to cause the processor to provide an indication that evidence of an undesirable predetermined compound fingerprint data is present in said spectral pattern data.

* * * * *

UNITED STATES PATENT AND TRADEMARK OFFICE

CERTIFICATE OF CORRECTION

PATENT NO. : 6,524,803 B2
DATED : February 25, 2003
INVENTOR(S) : Overney et al.

It is certified that error appears in the above-identified patent and that said Letters Patent is hereby corrected as shown below:

Column 6,
Line 49, " [illegible]:[illegible] " should be -- $\epsilon:\epsilon$ --.

Line 50, 54 and 56, " [illegible] " should be -- $\epsilon$ --.

Column 8,
Lines 28-31, the equation should be:

--
$$\lambda_c = I_c * p(C)^{-1} / \Sigma_i(I_{c(i)} * p(C(i))^{-1} + I_{residual} * p(C_{residual})^{-1})$$
$$\lambda_{residual} = I_{residual} * p(C_{residual})^{-1} / \Sigma_i(I_{c(i)} * p(C(i))^{-1} + I_{residual} * p(C_{residual})^{-1})$$
--

Signed and Sealed this

Third Day of August, 2004

JON W. DUDAS
*Acting Director of the United States Patent and Trademark Office*